(12) United States Patent
Fink et al.

(10) Patent No.: US 7,654,738 B2
(45) Date of Patent: Feb. 2, 2010

(54) CABLE GUIDING FOR A CEILING SUPPORT OF AN X-RAY DEVICE

(75) Inventors: Henning Fink, Ammersbek (DE); Uwe Meyer-Douque, Hamburg (DE); Horst-Hartwig Schwieker, Hamburg (DE); Janos Csikos, Budapest (HU); Gyorgy Medgyesi, Budapest (HU)

(73) Assignee: Koninklijke Philips Electronics N.V., Eindhoven (NL)

( * ) Notice: Subject to any disclaimer, the term of this patent is extended or adjusted under 35 U.S.C. 154(b) by 138 days.

(21) Appl. No.: 11/817,689

(22) PCT Filed: Mar. 6, 2006

(86) PCT No.: PCT/IB2006/050689

§ 371 (c)(1),
(2), (4) Date: Sep. 4, 2007

(87) PCT Pub. No.: WO2006/095301

PCT Pub. Date: Sep. 14, 2006

(65) Prior Publication Data

US 2008/0247516 A1    Oct. 9, 2008

(30) Foreign Application Priority Data

Mar. 7, 2005    (EP) .................... 05101728

(51) Int. Cl.
*H05G 1/06*    (2006.01)

(52) U.S. Cl. ..................................... 378/194

(58) Field of Classification Search ............... 378/194, 378/197
See application file for complete search history.

(56) References Cited

U.S. PATENT DOCUMENTS 3,037,119 A * 5/1962 Kizaur et al. ............... 378/194
3,118,066 A   1/1964 Thomas et al.
3,902,070 A   8/1975 Amor, Jr. et al.

(Continued)

FOREIGN PATENT DOCUMENTS

EP    1066794 A2    1/2001

(Continued)

OTHER PUBLICATIONS

Igus, "igus Energy Chain® Systems" [online], Oct. 14, 2003, [retrieved on Mar. 23, 2009]. Retrieved from the Internet: <http://web.archive.org/web/20031014154954/http://www.aboveboardelectronics.com/igus/echain/index.html>.*

*Primary Examiner*—Chih-Cheng G Kao

(57) ABSTRACT

The invention relates to a ceiling support system for a movable component (7) of a diagnostic X-ray device (1). The system comprises a horizontally movable carriage (8), a crane (9) attached to the carriage (8), which crane (9) is vertically extensible and contractible by means of telescoping sections (10), and at least one flexible electrical cable (17) for the power supply and/or for the control of the movable component (7). In order to provide such a ceiling support system with improved movability of the X-ray tube and/or the X-ray image detector, the invention suggests that the electrical cable (17) is led from the carriage (8) through the telescoping sections (10) of the crane (9), wherein a cable drum (18) is arranged at the top end of the crane (9) for winding the electrical cable (17) during vertical movement of the component (7).

13 Claims, 1 Drawing Sheet

U.S. PATENT DOCUMENTS

Figure 1:
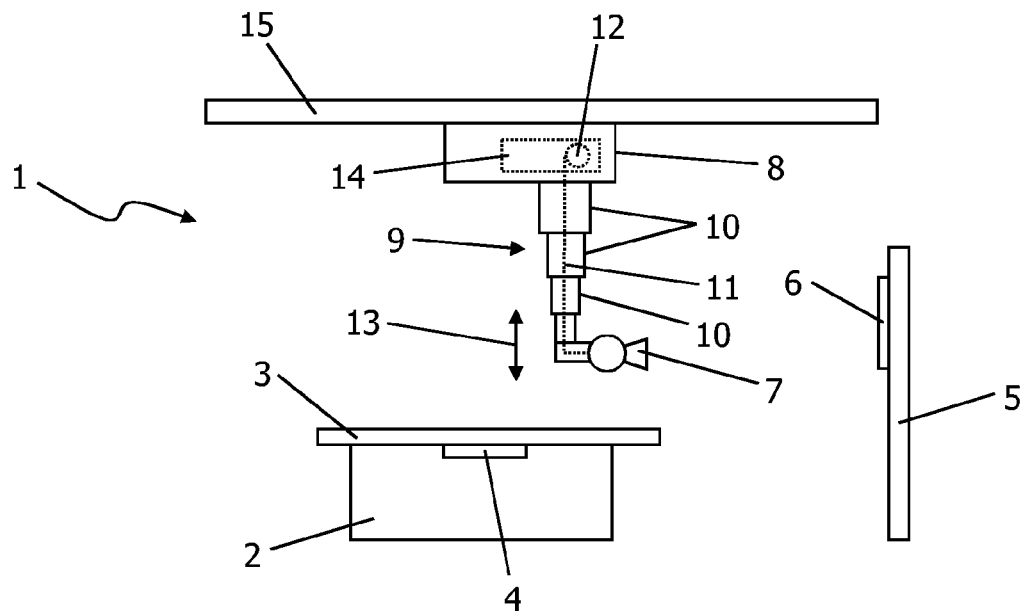

| | | | |
|---|---|---|---|
| 4,041,320 A | | 8/1977 | Amor, Jr. et al. |
| 4,435,830 A | * | 3/1984 | Suzuki et al. ................ 378/197 |
| 4,501,011 A | | 2/1985 | Hauck et al. |
| 6,065,710 A | * | 5/2000 | Richter et al. ............ 242/388.6 |

FOREIGN PATENT DOCUMENTS

WO     2004043261 A1    5/2004

* cited by examiner

CABLE GUIDING FOR A CEILING SUPPORT OF AN X-RAY DEVICE

The invention relates to a ceiling support system for a movable component of a diagnostic X-ray device, comprising a horizontally movable carriage, a crane attached to the carriage, which crane is vertically extensible and contractible by means of telescoping sections, and at least one flexible electrical cable for the power supply and/or for the control of the movable component.

Furthermore the invention relates to an X-ray apparatus comprising an X-ray source, an X-ray image detector in confronting relation to the X-ray source, and a ceiling support system for the X-ray source or the X-ray image detector.

In the field of medical diagnostic imaging, and particularly in the field of X-ray fluoroscopy and radiography, a wide spectrum of equipment is nowadays commercially available. In a conventional X-ray system, as it is for example known from U.S. Pat. No. 4,435,830, the patient is supported during an examination on a radiographic-fluoroscopic table comprising an X-ray image detector, e.g. a normal X-ray film, an electronic X-ray image intensifier, or a digital X-ray flat detector. An overhead X-ray source, e.g. a conventional X-ray tube, directs a beam of radiation through the patient to the X-ray image detector underneath the patient. The X-ray source is mounted on a ceiling support comprising a tube crane to enable vertical and horizontal movement of the X-ray source. A conventional ceiling support system of this type is for example described in the publication WO 2004/043261 A1. Depending on the respective part of the body of the patient to be examined, horizontal and vertical movability of the X-ray source and/or the X-ray image detector relative to the patient is necessary. The tube crane of the conventional X-ray apparatus is extensible and contractible by means of telescoping sections. These telescoping sections are telescopically movable by a wire rope wound around a pulley driven by a motor. The known systems usually further employ ceiling suspended guide rails for enabling horizontal movements of the X-ray tube.

In known X-ray systems cabling is required both for the power supply of the X-ray tube and the X-ray image detector and for electronic signal transmission to and from the back end electronics of the apparatus. Usually the corresponding cables are running from a room outlet to the component suspended on the ceiling support system of the X-ray device. The cables are guided through a flexible corrugated tube in order to allow for horizontal and vertical movement. This corrugated tube is conventionally fixed at a number of positions on the ceiling and on the crane.

It is a drawback of the known X-ray systems that the afore-described mode of cabling significantly obstructs the positioning of the movable components. This is mainly because of the weight of the electrical cables guided through the corrugated tubes and because of their resistance to flexion and torsion. A further problem is that the cables are often clamped together with the corrugated tubes between other parts of the X-ray apparatus and may get damaged.

Therefore it is readily appreciated that there is a need for an improved ceiling support system for X-ray devices in order to enable unobstructed horizontal and/or vertical movement of components of the X-ray device. It is consequently the main objective of the invention to provide such a ceiling support system with improved movability of the X-ray tube and/or the X-ray image detector.

In accordance with the present invention, a ceiling support system for a movable component of a diagnostic X-ray device is disclosed, comprising a horizontally movable carriage, a crane attached to the carriage, which crane is vertically extensible and contractible by means of telescoping sections, and at least one flexible electrical cable for the power supply and/or for the control of the movable component. The electrical cable is led from the carriage through the telescoping sections of the crane, wherein a cable drum is arranged at the top end of the crane for winding the electrical cable during vertical movement of the component.

With the ceiling support system of the invention, the electrical cable connecting the movable component of the X-ray device with the back end electronics is guided through the telescoping sections of the crane. Thus the cable cannot get tangled up and no obstruction can occur during vertical movements. A further advantage is that the electrical cable cannot be clamped and/or damaged inside the crane. The cable drum is winding the electrical cable such that a well-defined strain is put on the cable and the risk of damages is significantly reduced. The resistance of the cable to flexion and torsion can also not hamper the stroke of the component suspended on the ceiling support system because the cable is always in an elongated state inside the crane.

With the ceiling support system of the invention provision may be made for a motor for automatically lifting or lowering the component mounted on the crane. It is an important aspect of the invention that this motor may also be used to drive the cable drum. The vertical movement of the crane and the winding of the cable can be synchronized very simply in this way. This makes the realization of a servo assisted lifting and lowering operation of the ceiling support system significantly less complicated as compared to the conventional devices. The telescoping sections of the ceiling support system according to the invention may be vertically movable by means of a rope, wherein the rope is wound around a pulley arranged at the top end of the crane. The motor is driving this pulley and the cable drum for winding the electrical cable during vertical movements. The component of the X-ray device suspended on the crane, e.g. the X-ray source or the X-ray image detector, is moved by the motive force of the motor.

In accordance with a preferred embodiment of the ceiling support system of the invention, the electrical cable is guided in a first flexible cable carrier in the form of a chain consisting of a plurality of hingedly joined chain links in order to enable horizontal movement of the carriage, the chain being aligned in parallel with ceiling mounted guide rails on which the carriage is movable suspended. Such cable carriers are commercially available at low cost under the trade name "Energy Chain". These cable carriers guide and protect the moving cables without obstructing the movement and without the risk of damages. The use of an Energy Chain is therefore superior to the above-described conventional solutions employing a simple corrugated tube fixed at a number of arbitrarily selected positions along the supporting elements of the X-ray apparatus. Furthermore, it is advantageously possible to "hide" the Energy Chain underneath the profiles of the guide rails, such that they are completely enclosed within the constructional parts of the ceiling support system.

With the ceiling support system of the invention it is advantageous to make provision for a cable connection between the hub and the rotating outer diameter of the cable drum, which cable connection is guided through a second flexible cable carrier. A further Energy Chain of the type described above can be used for this purpose. One end of the chain is fixed near the hub of the cable drum while the other end is rotating together with the cable drum during vertical movements of the component suspended on the support system. Depending on the direction of the movement the chain closes or opens similar to a coil spring. In this way the connection to the cable wound up on the cable drum can be realized in a straightforward and cost-effective manner.

In accordance with the invention it is advantageous if the electrical cable is led out of the crane of the ceiling support system at its bottom end in a horizontal direction. This makes sure that the cable is only bent but not distorted when the moving component is rotated about the vertical axis of the crane.

Figure 2:
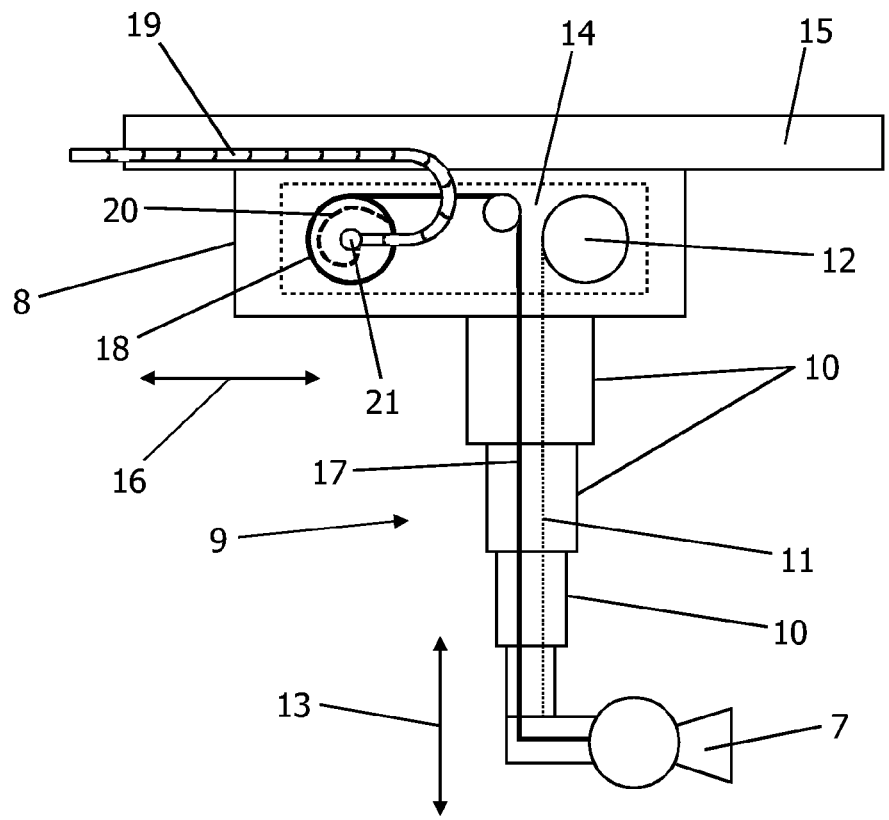

The following drawings disclose preferred embodiments of the present invention. It should be understood, however, that the drawings are designed for the purpose of illustration only and not as a definition of the limits of the invention. In the drawings FIG. 1 illustrates an X-ray device according to the invention;

FIG. 2 shows schematically the ceiling support system of the X-ray device depicted in FIG. 1.

With reference to FIG. 1 and FIG. 2, an X-ray device 1 in accordance with the present invention is described. The X-ray device 1 comprises a table 2 with a table top 3 for supporting a patient during an examination. The table 2 has a receptacle 4 for an X-ray film. Furthermore, provision is made for a wall stand 5 also comprising a receptacle 6 for an X-ray film. This wall stand 5 can be used for examination of a patient in a standing position. An overhead X-ray source 7 directs a beam of radiation through the patient to the X-ray film underneath or behind the patient. The X-ray source 7 is mounted on a ceiling support system to support the X-ray source 7 and to enable vertical and horizontal movement of the X-ray source 7. The ceiling support system comprises a horizontally movable carriage 8 and a tube crane 9 attached to the carriage 8. The tube crane 9 of the depicted X-ray apparatus 1 is extensible and contractible by means of telescoping sections 10. These telescoping sections 10 are telescopically movable by a wire rope 11 guided through the tube crane 9 and wound around a pulley 12. The X-ray source 7 can be lifted or lowered (as indicated by arrow 13) by means of a motor drive 14. The carriage 8 is attached to ceiling-mounted guide rails 15 for enabling horizontal movement (as indicated by arrow 16).

FIG. 2 shows the ceiling support system in greater detail. Provision is made for a flexible cable 17 for the power supply and for the remote control of the X-ray source 7. The cable 17 is led from the carriage 8 through the telescoping sections 10 of the crane 9 and is connected to the X-ray source 7. A cable drum 18 is arranged in the carriage 8 over the top end of the crane 9 for winding the electrical cable 17 during vertical movements of the X-ray source 7. The motor 14 is driving the pulley 12 and the cable drum 18 synchronously in order to make sure that the cable 17 is always in an elongated state inside the crane 9 and can therefore not obstruct its extension or contraction. Outside the carriage 8 the cable 17 is guided in a first flexible cable carrier 19. The cable carrier 19 is a so-called Energy Chain aligned in parallel with the ceiling mounted rails 15. Provision is made for a further Energy Chain 20 as a second flexible cable carrier. The cable 17 is guided through the Energy Chain 20 from the hub 21 to the outer diameter of the cable drum 18. The Energy Chain 20 behaves like a spring coil and opens or contracts depending on the direction of rotation of the cable drum 18 during vertical movement 13. The electrical cable 17 leaves the crane 9 at its bottom end in a horizontal direction in order to facilitate rotation of the X-ray source 7 around the vertical axis of the crane 9.

The invention claimed is:

1. Ceiling support system for a movable component (7) of a diagnostic X-ray device (1), comprising:
    a horizontally movable carriage (8);
    a crane (9) attached to the carriage (8), which crane (9) is vertically extensible and contractible by telescoping sections (10) vertically movable by a rope (11) wound around a pulley (12) arranged at the top end of the crane (9); and
    at least one flexible electrical cable (17) for a power supply and/or for control of the movable component (7),
    wherein the electrical cable (17) is led from the carriage (8) through the telescoping sections (10) of the crane (9), wherein a cable drum (18) is arranged at the top end of the crane (9) for winding the electrical cable (17) during vertical movement of the component (7), and wherein a motor (14) synchronously drives the pulley (12) and the cable drum (18).

2. Ceiling support system according to claim 1, wherein the electrical cable (17) is guided in a first flexible cable carrier (19) in the form of a chain consisting of a plurality of hingedly joined chain links in order to enable horizontal movement of the carriage (8), the chain being aligned in parallel with ceiling mounted guide rails (15) on which the carriage (8) is movably suspended.

3. Ceiling support system according to claim 1, wherein further provision is made for a cable connection between a hub (21) and the rotating outer diameter of the cable drum (18), which cable connection is guided through a second flexible cable carrier (20) in the form of a chain consisting of a plurality of hingedly joined chain links.

4. Ceiling support system according to claim 1, wherein the electrical cable (17) is led out of the crane (9) at its bottom end in a horizontal direction.

5. X-ray apparatus comprising an X-ray source (7), an X-ray image detector (4, 6) in confronting relation to the X-ray source (7), and a ceiling support system for vertical and/or horizontal movement of the X-ray source (7) or the X-ray image detector (4, 6), wherein the ceiling support system comprises a horizontally movable carriage (8), a crane (9) attached to the carriage (8), which crane (9) is vertically extensible and contractible by telescoping sections (10) vertically movable by a rope (11) wound around a pulley (12) arranged at the top end of the crane (9), and at least one flexible electrical cable (17) for a power supply and/or for control of the X-ray source (7) or the X-ray image detector (4, 6), wherein the electrical cable (17) is led from the carriage (8) through the telescoping sections (10) of the crane (9), wherein a cable drum (18) is arranged at the top end of the crane (9) for winding the electrical cable (17) during vertical movement of the X-ray source (7) or the X-ray image detector (4, 6), and wherein a motor (14) synchronously drives the pulley (12) and the cable drum (18).

6. X-ray apparatus according to claim 5, wherein the electrical cable (17) is guided in a first flexible cable carrier (19) in the form of a chain consisting of a plurality of hingedly joined chain links in order to enable horizontal movement of the carriage (8), the chain being aligned in parallel with ceiling mounted guide rails (15) to which the carriage (8) is movably suspended, wherein further provision is made for a cable connection between a hub (21) and the rotating outer diameter of the cable drum (18), which cable connection is guided through a second flexible cable carrier (20) in the form of a chain consisting of a plurality of hingedly joined chain links.

7. X-ray apparatus, comprising:
an X-ray component; and
a ceiling support system for vertical moving the X-ray component, wherein the ceiling support system includes
a crane vertically movable relative to the ceiling support system, the X-ray component being mounted to the crane,
a pulley for vertically moving the crane,
a flexible electrical cable in electrical communication with the X-ray component,
a cable drum for winding the flexible electrical cable during a vertical movement of the crane, and
a motor for synchronously driving the pulley and the cable drum.

8. The X-ray apparatus of claim 7, wherein the X-ray component is mounted to a bottom end of the crane.

9. The X-ray apparatus of claim 7, wherein the pulley and the cable drum are arranged at a top end of the crane.

10. The X-ray apparatus of claim 7, wherein the flexible electrical cable extends through the crane and out of a bottom end of the crane in a horizontal direction.

11. The X-ray apparatus of claim 7,
wherein the ceiling support system further includes a carriage horizontally movable relative to the ceiling support system; and
wherein the crane is attached to the carriage.

12. The X-ray apparatus of claim 7, wherein the X-ray component is an X-ray source.

13. The X-ray apparatus of claim 7, wherein the X-ray component is an X-ray image detector.

* * * * *